United States Patent [19]

Doyle

[11] Patent Number: 5,991,029
[45] Date of Patent: Nov. 23, 1999

[54] ATTENUATED TOTAL REFLECANCE PROBE EMPLOYING LARGE INCIDENCE ANGLES

[75] Inventor: Walter M. Doyle, Laguna Niguel, Calif.

[73] Assignee: Axiom Analytical, Inc., Irvine, Calif.

[21] Appl. No.: 09/055,392

[22] Filed: Apr. 6, 1998

[51] Int. Cl.⁶ .............................. G01N 21/01; G01B 9/02
[52] U.S. Cl. ...................................... 356/346; 250/339.11
[58] Field of Search ............................ 356/346, 51, 244; 250/339.11, 339.12, 341.2

[56] References Cited

U.S. PATENT DOCUMENTS

| | | | |
|---|---|---|---|
| 3,591,287 | 7/1971 | Hannis | 356/51 |
| 4,829,186 | 5/1989 | McLachlan et al. | 356/51 |
| 5,326,972 | 7/1994 | Codella | 250/339.11 |
| 5,773,825 | 6/1998 | Doyle | 250/339.11 |

OTHER PUBLICATIONS

Internal Reflection Spectroscopy, N.J. Hendrick, Mar. 1971, pp. 89–145.

*Primary Examiner*—Samuel A. Turner
*Attorney, Agent, or Firm*—Thomas J. Plante

[57] ABSTRACT

A sample immersion probe is disclosed which has an ATR (attenuated total reflectance) element at its tip. The ATR is so shaped that radiation exiting the probe will travel in paths parallel to radiation entering the probe. The angles of incidence of radiation on the ATR surface (or surfaces) which permit partial absorption by the sample material are greater than 45°. At least one of the ATR surfaces in contact with the sample has a fully reflecting coating which prevents radiation absorption by the sample at that location. The ATR shape may be symmetrical or non-symmetrical with respect to the axis of symmetry of the probe. The radiation entering the probe may be in a separate light guide (i.e., path) from the radiation exiting the probe; or the entering and exiting radiation may be in the same light guide (path).

10 Claims, 8 Drawing Sheets

ATTENUATED TOTAL REFLECANCE PROBE EMPLOYING LARGE INCIDENCE ANGLES

BACKGROUND OF THE INVENTION

This invention relates to the use of attenuated total reflectance (ATR) elements (e.g., probes) which provide spectral analysis of liquid samples. It relates particularly to the spectral analysis of liquids which require higher than usual angles of incidence of the rays which are reflected inside the ATR probes, and are subject to partial absorption by the sample.

Attenuated total reflectance is a widely used technique for spectrally analyzing liquids having absorptions which are too strong for convenient transmission analysis. This condition is commonly encountered in the infrared (IR) region of the spectrum—the spectral region which includes the fundamental frequencies or most molecular vibrations. The ATR has also found some use in the ultra-violet (UV) and visible regions, as in the analysis of dyes and other strongly absorbing substances which are soluble in water.

Over the years, a large number of ATR devices have been developed—including several by the present inventor. ATR probes generally fall into two categories: those employing cylindrical ATR rods (see FIG. 2 of U.S. Pat. No. 5,051,551), and those employing conical elements (see FIG. 8 of the same patent).

Both of these figures show optical rays which strike the interface between the ATR element and the analyte (sample) at an incidence angle of 45 degrees. The incidence angle is defined as the angle between the ray direction and the normal to the surface. A 45 degree incidence angle is often convenient. That angle is usually appropriate for the analysis of organics in the IR region. For the high index ATR materials available for use in the IR region, it is sufficiently above the critical angle to avoid significant data distortion.

The critical angle is defined as the smallest incidence angle for which an optical ray, in the absence of absorption, will be totally reflected at the interface. It is equal to $$\phi_c = \sin^{-1}(n_1/n_2)$$

where $n_1$ and $n_2$ represent the indices of refraction of the analyte and the ATR element, respectively. Typical organic materials have refractive indices around 1.5, while several common infrared ATR materials have indices equal to 2.4 or higher. For this particular combination, the critical angle is equal to 38.7°. The 45° angle often used is well beyond this.

For some applications, it is desirable-or even necessary-to use an incident angle larger than 45°. This can occur, even when using a relatively high index ATR material, if the analyte is very strongly absorbing, or has an especially high refractive index. In other cases, the use of a high index ATR material may be precluded by such considerations as vulnerability to chemical attack, or required spectral region for the analysis. For example, in the higher frequency portion of the IR region, both sapphire (n=1.8) and cubic zirconia (n~2.0) provide good chemical resistance and high optical transmission. But their relatively low indices necessitate the use of incidence angles greater than 45°. With the rod type ATR probe, this can be accomplished by altering the included angle of the rod end cones and/or the angle of the metallic reflecting cones. However, with the conical element ATR probe design, the situation isn't as simple.

Conical element ATR probes have a distinct advantage over the rod design for many industrial applications, in that they provide much higher transmission for a given probe diameter. However, since the ATR element also functions as a retroreflector, it is not possible to change the cone angle at will. One solution for this problem is to use more than two reflections. Examples corresponding to three and four reflections are shown in FIGS. 1 and 2. Three reflections with equal incidence angles will provide an incidence angle of 60° (see FIG. 1), while four reflections will result in 67.5° (see FIG. 2). A disadvantage of this approach is that, for a given incident beam diameter, the required probe diameter increases rapidly as the number of reflections increases.

Three reflection probes employing sapphire elements have been used for the UV and visible analysis of water solutions of strongly absorbing substances such as dyes. Since water has a low index (n=1.33), the critical angle is well below 60°:

$$\phi_c = \sin^{-1}(1.33/1.8) = 47.6°$$

The difficulty arises when one attempts to use these same probes to analyze organic materials, many of which have very strong absorbances in the UV spectral region. Such materials often have average refractive indices around 1.5. With an ATR element having an index of 1.8, the critical angle will be 56.4°. While this is still below 60°, it is close enough to give rise to significant band distortion, especially when one takes into account the range of angles which characterize a typical incoherent optical beam. But this isn't the whole story. Rather than remaining fixed at its average value, the refractive index of a substance departs substantially from this value in the vicinity of a strong absorption band. This situation is illustrated by FIGS. 3a, 3b, and 3c. Since the index is elevated on the longer wavelength side of the band, the critical angle will be higher and the penetration depth greater. The result will be a skewing of the measured band (see FIG. 3c). The only solution to this problem is a further increase in incidence angle.

As noted earlier, one solution to the above problem would be to use a four reflection ATR element as shown in FIG. 2. However, this would substantially increase the required probe diameter for a given input beam area. It would also increase the travel distance of the beam in the element, giving rise to greater signal loss due to beam spread (vignetting) and possibly bulk absorption.

SUMMARY OF THE INVENTION

A probe is provided in which the ATR element acts as a retroreflector, in the sense that it returns an optical beam on a path parallel to its incoming direction. At the same time, the angle of incidence is set at a high enough value to avoid absorbance nonlinearity and band distortion. Finally, these objectives are accomplished while minimizing the overall probe diameter for a given optical path area.

In order to combine those desired functions, the present invention employs a probe which has (a) an ATR element with the property of returning an incident beam on a path parallel to its incoming direction, and (b) two or more reflecting surfaces which have nonequal optical incidence angles and at least one of which, i.e., the one having the lowest incidence angle surface, is covered by a reflective coating.

DETAILED DESCRIPTION OF SPECIFIC EMBODIMENTS

Figure 1:
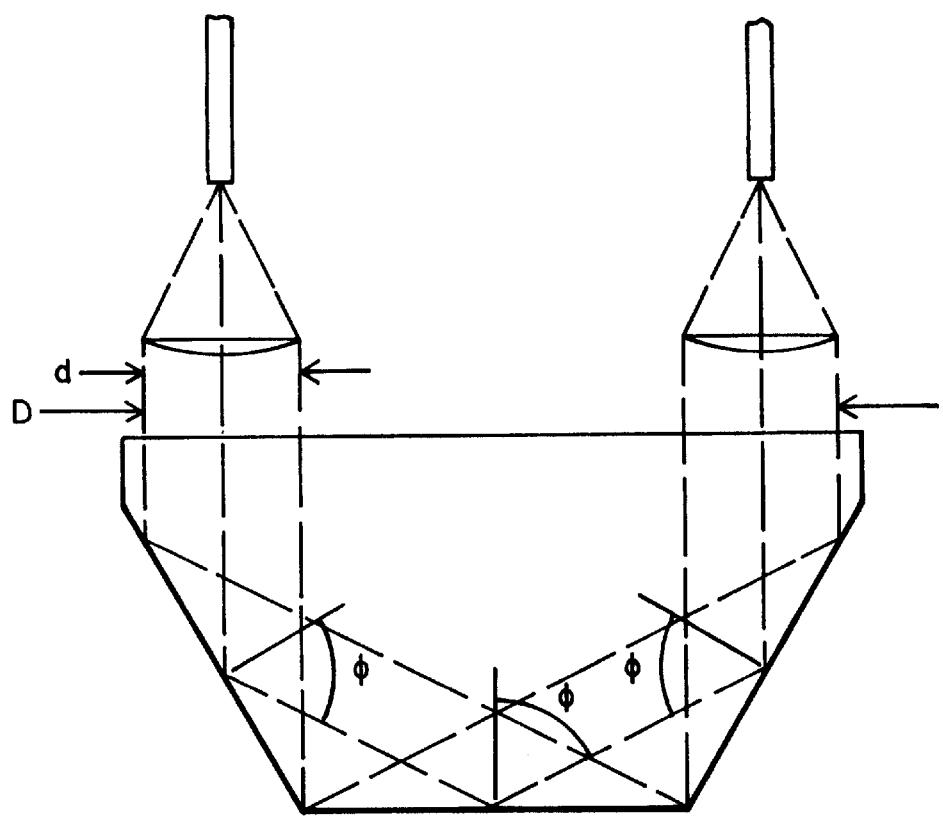
FIGS. 1 and 2 (referred to above) illustrate, respectively, structures having three and four beam reflecting surfaces.
Figure 2:
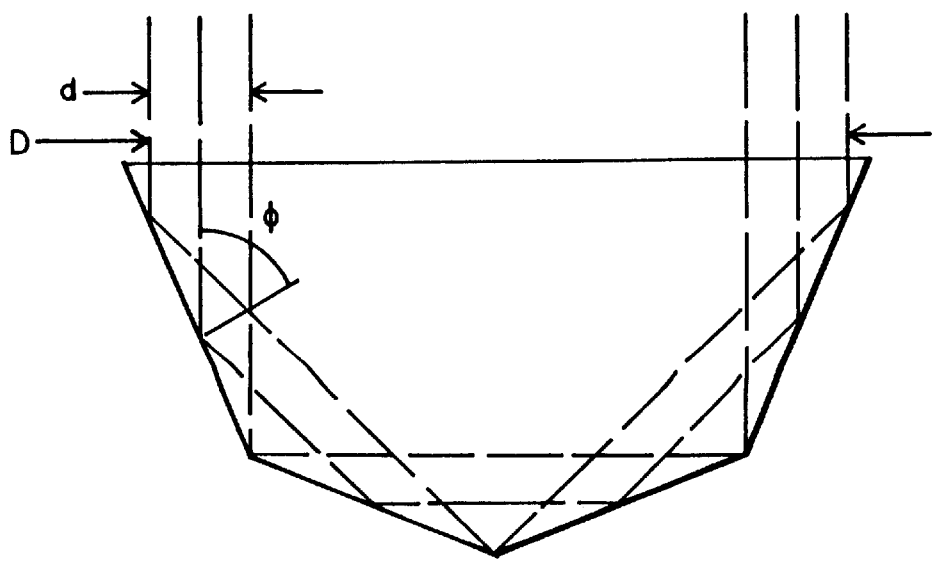
Figure 3A:
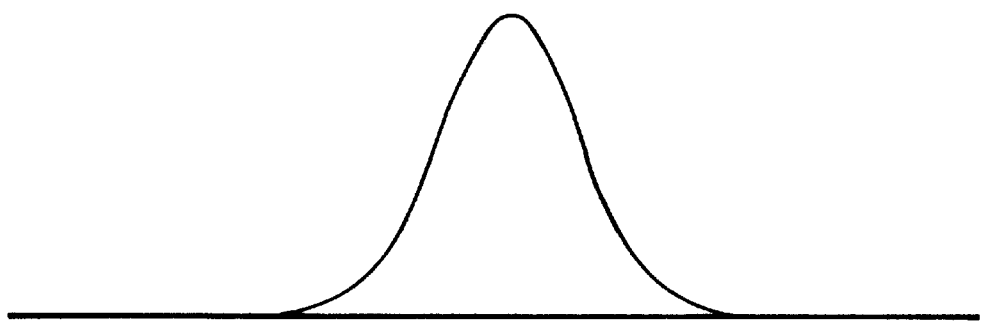
FIGS. 3a, 3b and 3c show waveforms which illustrate the possible skewing of the measured band by an incidence angle which is too small.
Figure 3B:
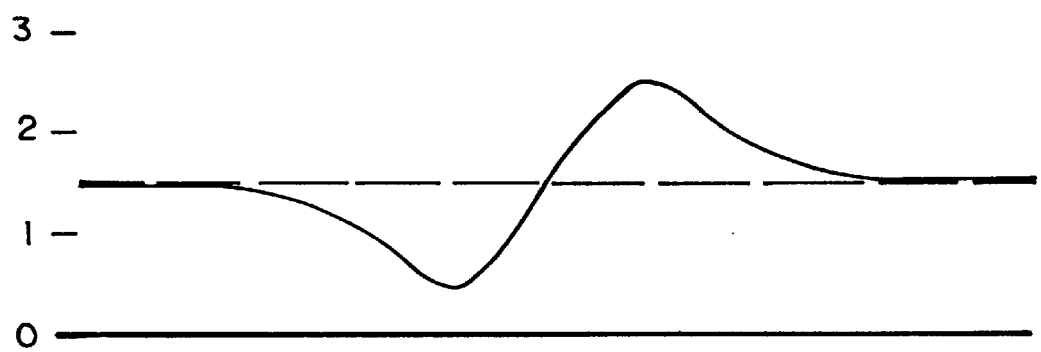
Figure 3C:
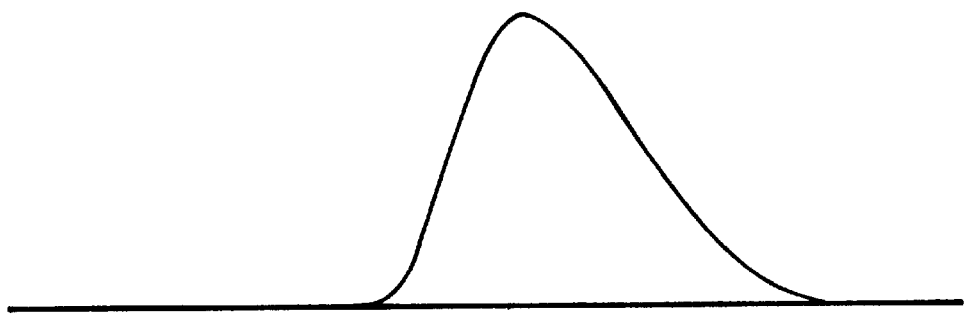
Figure 4:
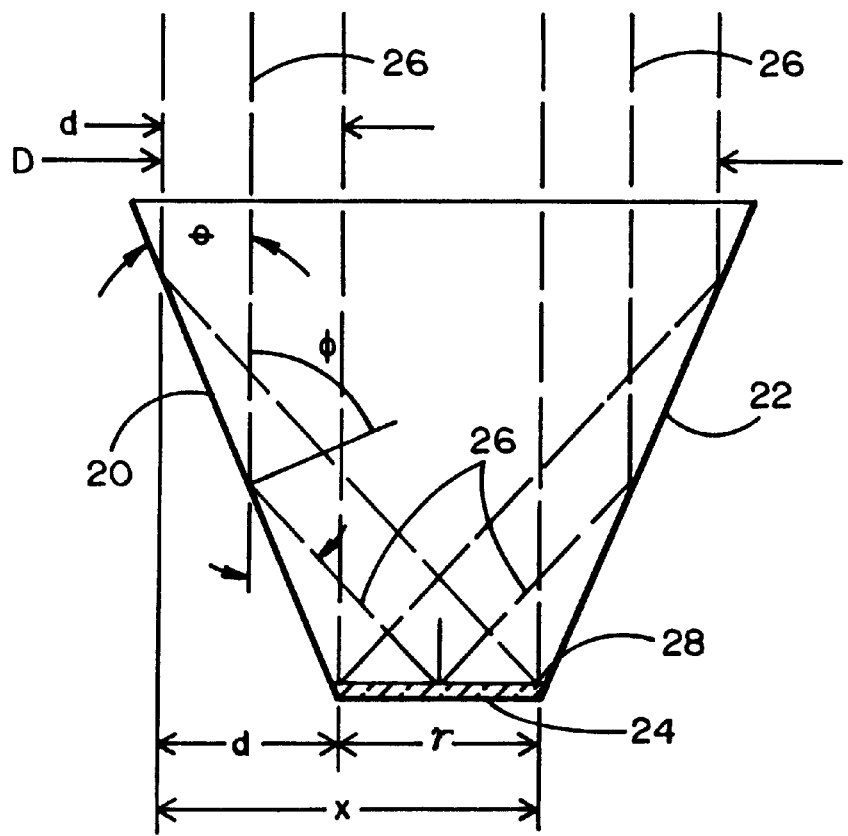
FIG. 4 is a partly sectional view of an embodiment of the invention having three reflections in a probe tip.

FIG. 4 shows one embodiment of the invention. This case utilizes three reflections, the first and third of which are at surfaces 20 and 22, which make equal but opposite angles with the incident beam direction. The second reflection is at a surface 24, which is perpendicular to the incoming beam direction. The first and third surfaces 20 and 22 could be separate inclined planes or included in a continuous conical surface.

The key to this embodiment is that it will always return the beam (e.g., beam 26) in a direction parallel to its entering direction, independent of the angle of inclination of the first and third surfaces. Thus, the inclination can be varied to set the incidence angle at these two surfaces 20 and 22 at any desired value. Of course, if the incidence angle at these surfaces is set higher than 60°, the incidence angle at the second surface 24 will be less than 60°.

This introduces the second aspect of the invention. The second surface 24 is covered with a suitable reflective coating 28, so that it will be highly reflective independently of the incidence angle. An aluminum coating with a protective overcoat of sapphire will suffice for many applications.

If the angle of incidence at the first and third surfaces 20 and 22 is set at less than 60°, the angle at the second surface 24 will be greater. In that case, the first and third surfaces may be aluminized, providing at surface 24 a single reflection ATR element, having any desired angle of incidence.

The inventive concepts can be implemented with various structures. Consider first structures which exhibit symmetry with respect to reflection through an axis parallel to the direction of the incoming beam. Any such structure employing an odd number of reflections will exhibit the required retroreflection characteristic. The desired goal can be accomplished by using such a structure in which the angles of incidence are not all equal, and by reflectively coating those surfaces having the lower incidence angles.

Figure 5:
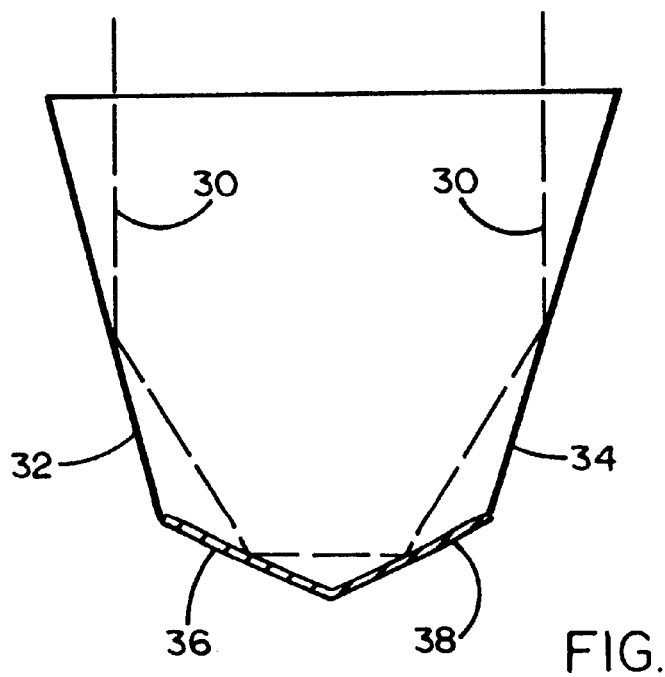
FIG. 5 is a partly sectional view of an embodiment of the invention having four reflections in a probe tip.

An element having an even number of reflections can also meet the requirements. However, in that case, retroreflection is not automatic. Under the assumed mirror symmetry conditions, this can be accomplished by choosing the surface angles so that the optical ray segment which passes through the axis of symmetry is perpendicular to that axis. Such an embodiment is shown in FIG. 5, in which the ray 30 is reflected at four surfaces, two of which, 32 and 34, permit sample radiation absorption, and two of which, 36 and 38, are coated to prevent sample radiation absorption.

Figure 6:
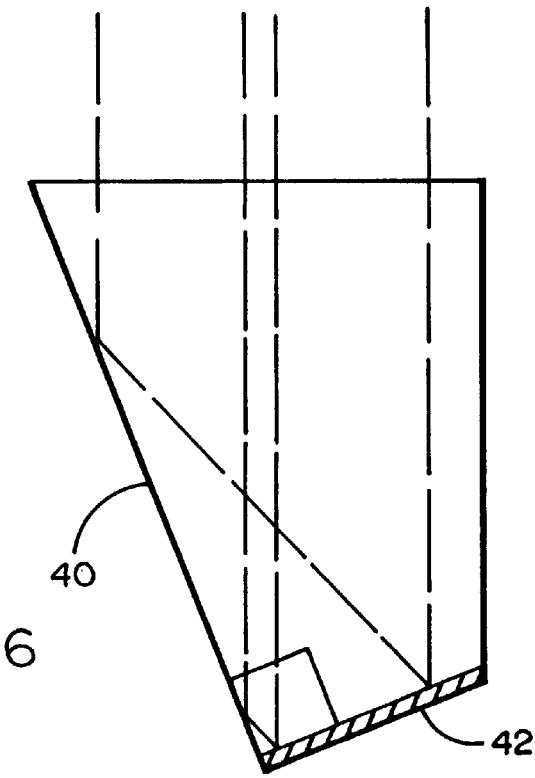
FIG. 6 is a partly sectional view of an embodiment of the invention having a non-symmetric probe tip shape.

A further expansion of the invention embodiments is obtained by relaxing the requirement for symmetry with respect to reflection through the axis. One such example is shown in FIG. 6, a two reflection design employing plane surfaces 40 and 42. As long as the two surfaces 40 and 42 have an included angle of 90°, they will act as a rooftop retroreflector, independent of the angle that each one makes with the incident beam direction. (For this example, it is required that the normals to the two surfaces 40 and 42 lie in the plane of incidence.) The desired goal can thus be achieved by inclining one of the two surfaces, 40, to provide the desired incidence angle, and aluminiziig the other surface, 42.

Thus far, structures have been considered in which the incoming and outgoing beams are separated in space and possibly enclosed in separate lightguides. However, the invention also is intended for probe structures in which the incoming and outgoing beams are contained within the same lightguide, and are separated by a beamsplitter at some point in the system. In such structures, it is necessary to include some measures to make sure that reflections from the rear surface of the ATR element do not reach the IR detector. (See U.S. Pat. No. 5,459,316 for further discussion.)

Figure 7:
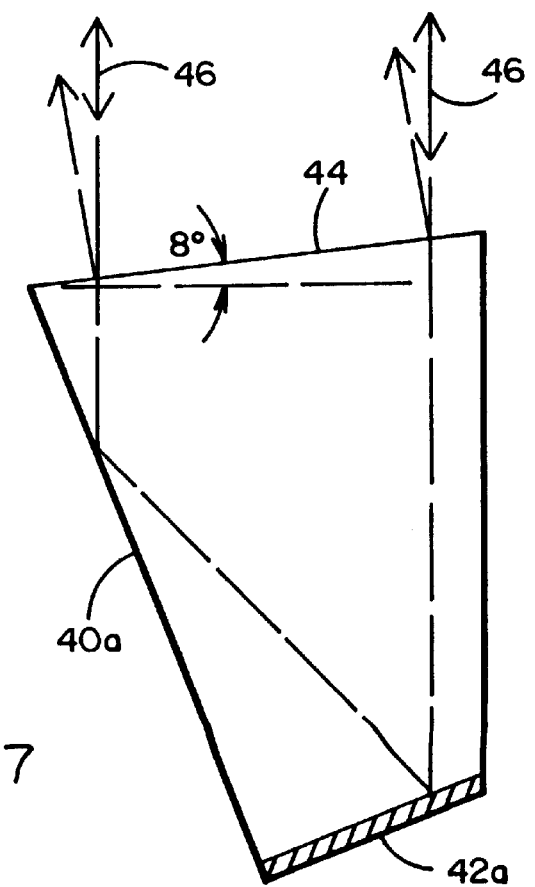
FIG. 7 is a partly sectional view of an embodiment of the invention having a probe tip similar to FIG. 6, combined with an ATR element rear surface which avoids reflection from that surface into the detector.
Figure 8:
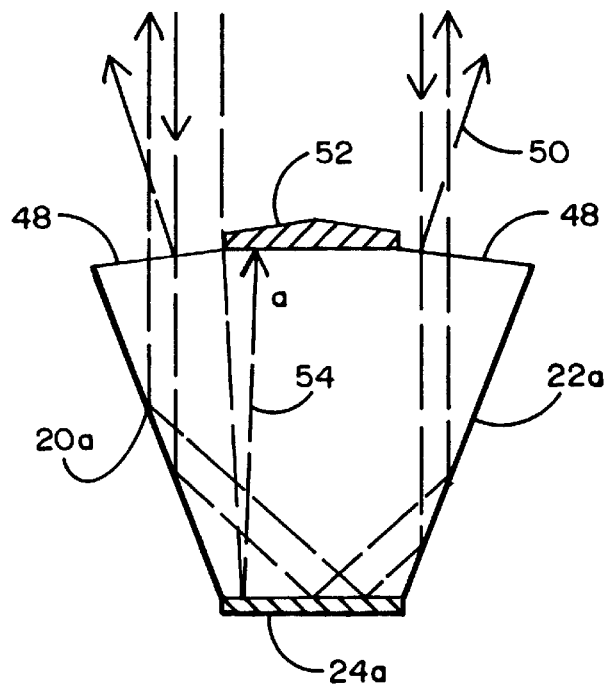
FIG. 8 is a partly sectional view of an embodiment of the invention having a structure similar to FIG. 4 modified in the manner of FIG. 7.

FIGS. 7, 8, and 9 illustrate examples of the invention in which light reflected from the rear surface of the ATR element is directed into a range of angles sufficiently far from the system axis, so that it will not be focused on the detector in the spectrometer system.

FIG. 7 is the same as FIG. 6 (note surfaces 40a and 42a), except that the rear surface 44 is angled so that the angle of incidence of axial rays 46 on surface 44 will be at least 5 degrees, preferably about 8 degrees. The rear surface reflected component of such rays will then be at least 10 degrees from the axis of the rays.

The embodiment of FIG. 8 is related to that of FIG. 4, having three reflecting surfaces 20a, 22a and 24a. However, the rear surface 48 of the ATR element has been modified to deflect reflected light (e.g., ray 50) away from the axis. Considering the case where the ATR element shape is circular in cross section, the rear surface 48 would be a shallow cone. In addition, the central area 52 of this surface is blackened (or otherwise made opaque) so that rays which miss the conical surface and strike the fully reflecting surface directly (such as the ray labeled 54) will not be returned to the detector.

Figure 9A:
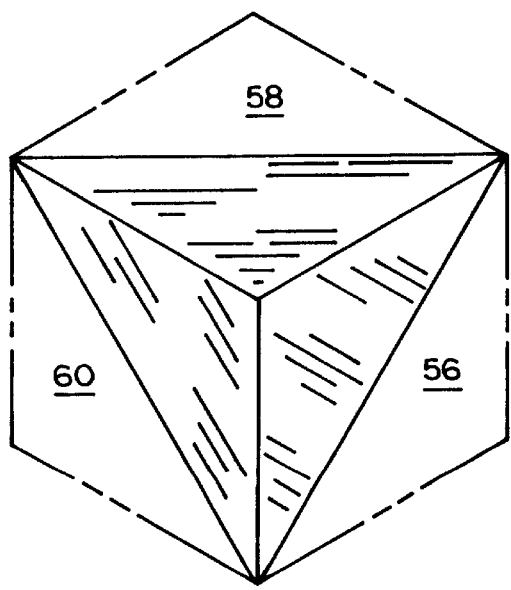
FIGS. 9a and 9b show a cube-shaped ATR probe tip, formed as a cube corner, in which light rays reflect off all three sides of the cube.
Figure 9B:
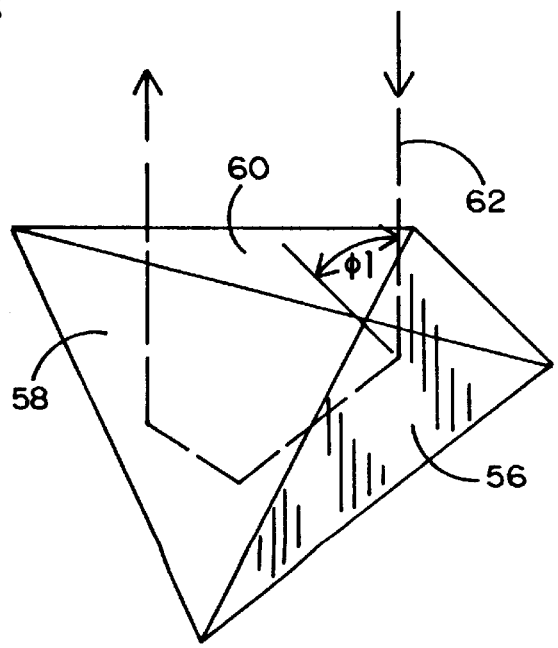

In FIGS. 9a and 9b, the element is a cube corner retroreflector. FIG. 9a shows a full cube, from which the ATR element of FIG. 9b is figuratively cut out. Such devices employ three reflecting surfaces, 56, 58, and 60, each of which makes a 90° angle with the other two. If the retroreflector is positioned so that its surfaces are symmetrical with respect to the probe axis, a given ray, e.g., ray 62, will be reflected once at each surface and then will return on a path parallel to its direction of entry. The angle of incidence at each surface will be approximately 57°. If the element is tilted with respect to the axis (as shown in FIG. 8), the ray will still return on a parallel path, but the angles of incidence at the three surfaces will be different. In the case shown, the first incidence angle, $\phi_1$, is set at a value lower than 57°. The other two are assumed to be greater than 57°. In this case, the first surface 56 is metalized to fully reflect the ray 62.

Based on present knowledge, the embodiments shown in FIGS. 6 and 7 are preferred for commercial use. In comparing the two, the FIG. 6 embodiment has the advantage of better performance because the incoming and outgoing light rays are separated. However, the dual light guide structure of FIG. 6 inherently has a larger diameter probe than that of FIG. 7, in which the incoming and outgoing light rays are in the same lightguide path. In the device of FIG. 7, separation of the incoming and outgoing rays occurs at a beamsplitter outside of the probe element. The smaller diameter probe of FIG. 7 is preferred in some situations.

Figure 10:
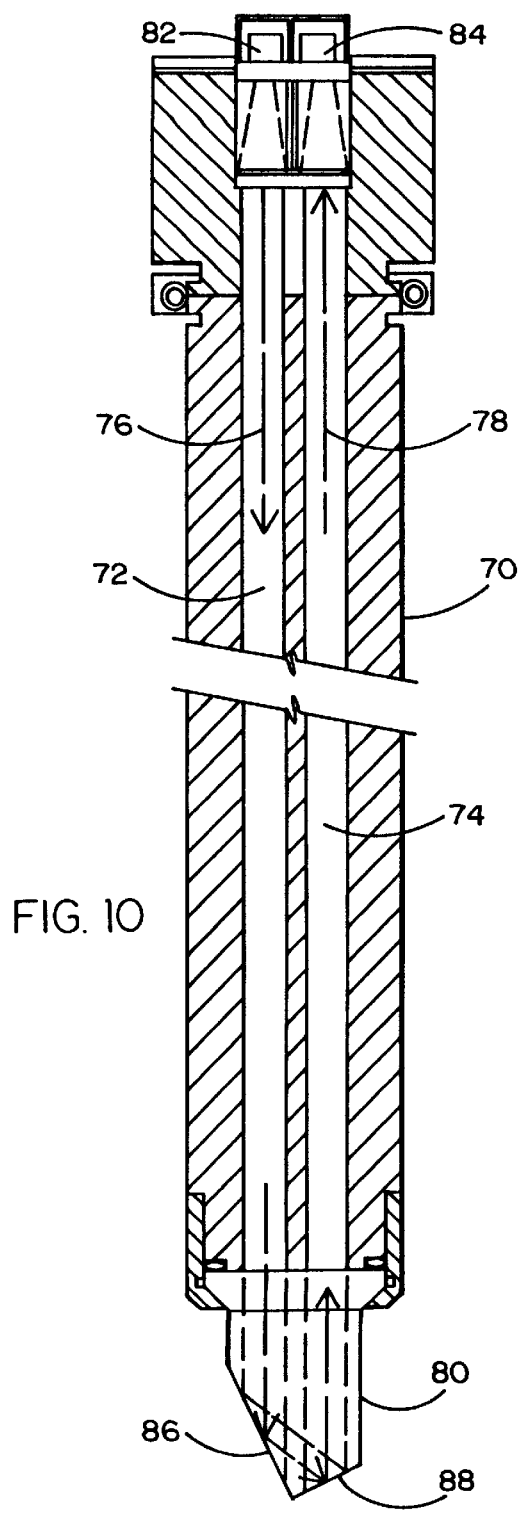
FIG. 10 is a partly sectional view of a probe having separate input and output light paths, adapted to be incorporated in a spectrometer system, and having at its tip an ATR element of the type shown in FIG. 6.

FIG. 10 shows, partly in section, the full length of an immersion probe 70 having separate light guides 72 and 74 for incoming and returning rays 76 and 78. The sample-contacting end of the probe 70 supports an ATR element 80 of the type shown in FIG. 6. At the other end of probe 70, two fiber optic connections 82 and 84 are used to connect the incoming and outgoing radiation to a spectrometer. Surface 86 of the ATR provides a sample absorption reflection, and surface 88 of the ATR provides a fully reflecting surface, which precludes radiation absorption by the sample.

Figure 11:
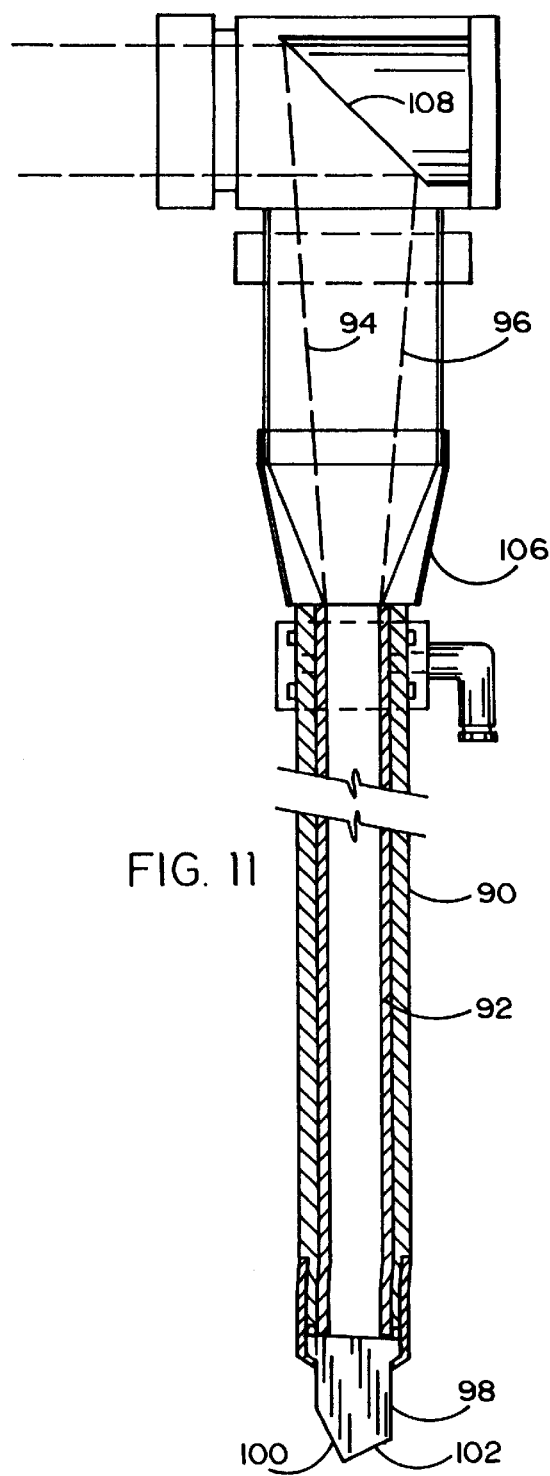
FIG. 11 is a partly sectional view of a probe having a single light transmission path, which incorporates the ATR element shown in FIG. 7, and which is adapted to be incorporated in a spectrometer system.

FIG. 11 shows, partly in section, the full length of an immersion probe 90 having a single light guide 92 for both incoming and outgoing rays 94 and 96. The ATR element 98, supported by probe 90, has a surface 100 which permits sample absorption of radiation, and a fully reflective surface 102 which precludes radiation absorption by the sample. The ATR element 98 in FIG. 11 is similar to the ATR element 80 in FIG. 10, except that rear surface 104 of element 98 is inclined, preferably 8°, to prevent rear surface reflection from reaching the detector.

Figure 12:
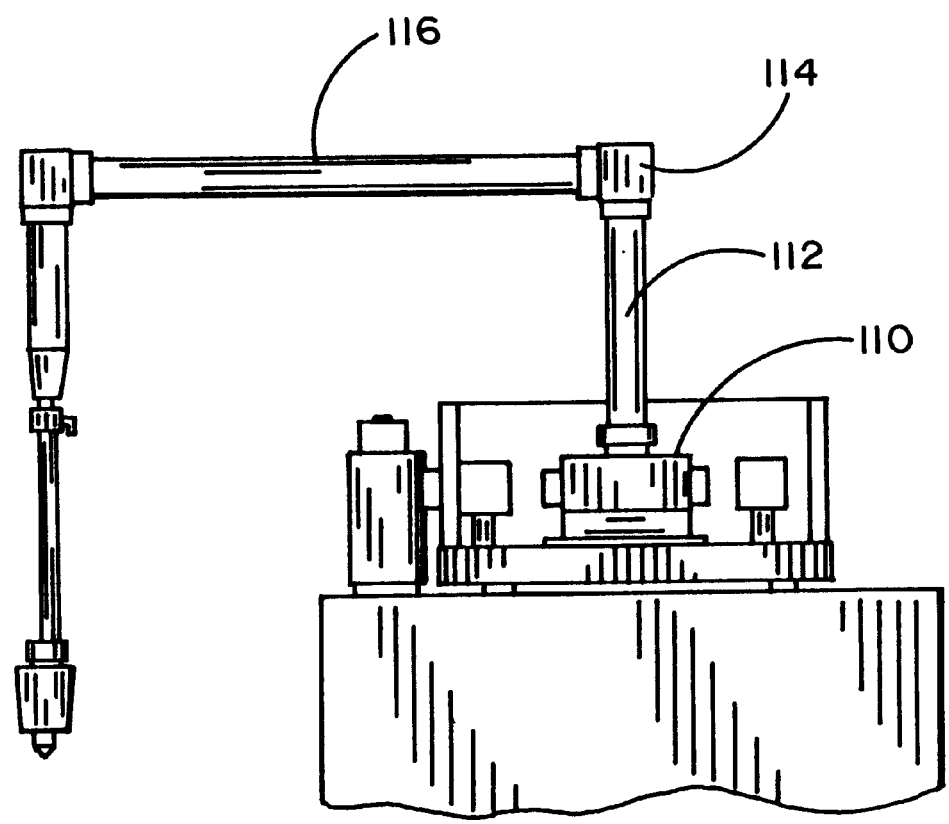
FIG. 12 shows a system in which a probe of the type shown in FIG. 11 is connected by an Axiot™ light guide system to a spectrometer.

The other end of probe 90 is supported by a probe coupler 106, which is connected to a fixture containing a parabolic focusing mirror 108. The incoming and outgoing radiation paths are separated by a beamsplitter 110, the exterior of which is shown in FIG. 12. The radiation path between beamsplitter 110 and probe coupler 106 is enclosed by Axiot™ light pipe structures 112-114-116, of the type shown in U.S. Pat. No. 5,054,869.

Figure 13:
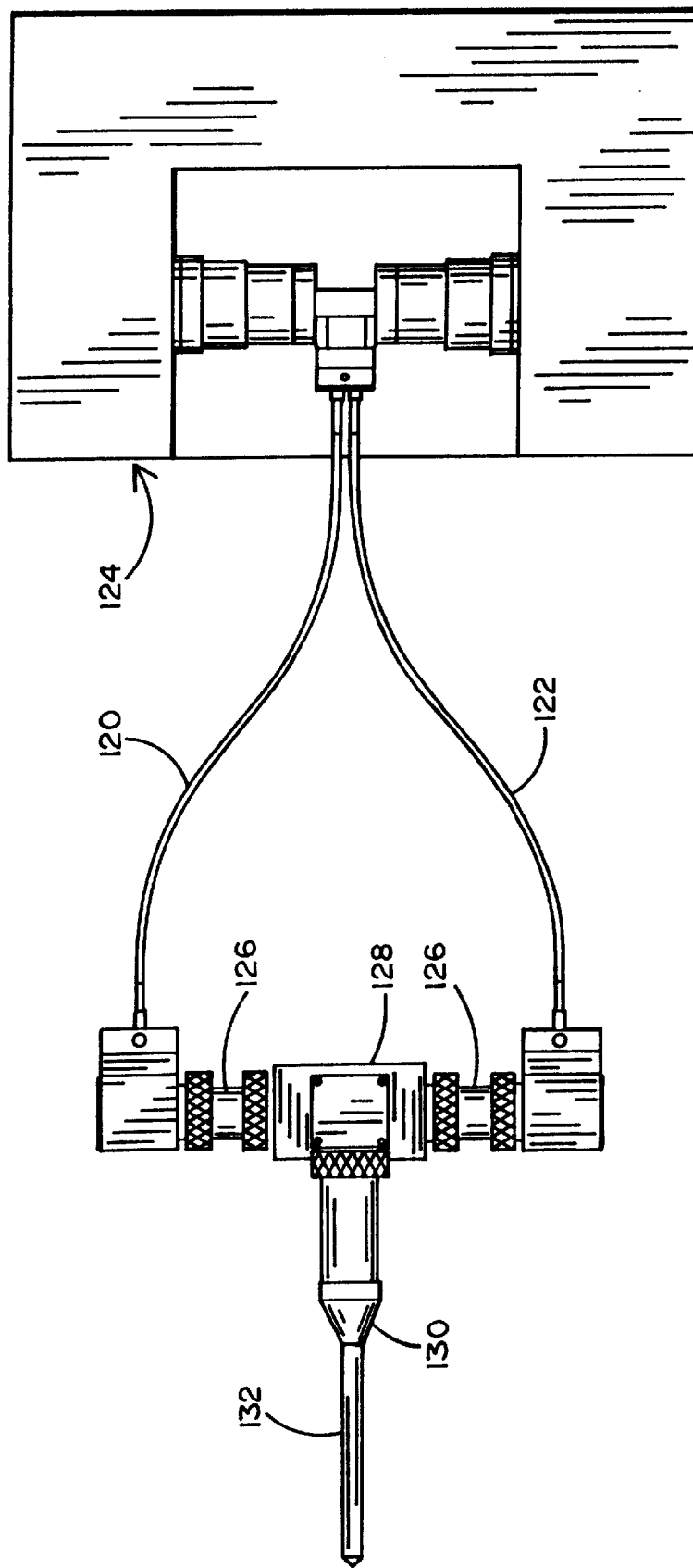
FIG. 13 illustrates a system in which fiber optic connections may be used to replace some of the Axiot™ connections of FIG. 12.

FIG. 13 illustrates a system in which an FTIR spectrometer is connected to a probe using a combination of fiber optic connections and Axiot connections. Two fiber optic cables 120 and 122 lead from an FTIR interferometer 124 to opposite ends of an Axiot assembly 126, which provides separate incoming and outgoing radiation paths to a beamsplitter 128, which is connected by a probe coupler 130 to an immersion probe 132.

From the foregoing description, it will be apparent that the apparatus embodiments disclosed in this application will provide the significant functional benefits summarized in the introductory portion of the specification.

The following claims are intended not only to cover the specific embodiments disclosed, but also to cover the inventive concepts explained herein with the maximum breadth and comprehensiveness permitted by the prior art.

What is claimed is:

1. For use in a spectral analysis system having a radiation source, an interferometer which receives radiation from the source, a container having a sample, and a detector which receives sample-modulated radiation, a sample immersion probe comprising:

an elongated light guide member which inputs incoming radiation from the interferometer, and outputs exiting radiation to the detector, the incoming and exiting radiation traveling along substantially parallel paths; and an ATR internal reflectance element located at the lower end of the probe and having a plurality of radiation reflecting surfaces; the radiation reflecting surfaces including at least two such surfaces which have different angles of incidence and at least one of which is a sample radiation absorption surface; and the radiation reflecting surface which has the lowest angle of incidence being a substantially fully reflecting surface in order to prevent radiation absorption by the sample at that surface.

2. The structure of claim 1 in which the ATR element has two reflecting surfaces, one of which provides a relatively high angle of incidence for sample radiation absorption.

3. The structure of claim 2 in which there is a 90° included angle between the radiation striking the sample radiation absorption surface and the radiation striking the substantially fully reflecting surface.

4. The structure of claim 1 in which the angles of incidence of the radiation on the surface of the ATR element are such as to cause the entering and exiting radiation to travel along substantially parallel paths.

5. The structure of claim 1 in which the ATR element has three reflecting surfaces, one of which is a substantially fully reflecting surface, and two of which are sample radiation absorption surfaces.

6. The structure of claim 1 in which the ATR element has four reflective surfaces, two of which are substantially fully reflecting surfaces, and two of which are sample radiation absorption surfaces.

7. The structure of claim 1 in which the elongated light guide member provides separated paths for the incoming and outgoing radiation.

8. The structure of claim 1 in which the elongated light guide member causes the incoming and outgoing radiation to travel in the same space.

9. The structure of claim 1 in which any ATR radiation reflecting surface which permits sample radiation absorption has an angle of incidence greater than 45°.

10. The structure of claim 1 in which any ATR reflecting surface which permits sample radiation absorption has an angle of incidence of at least 60°.

* * * * *